US010842877B2

(12) United States Patent
Van Spreuwel-Goossens (10) Patent No.: US 10,842,877 B2
(45) Date of Patent: Nov. 24, 2020

(54) METHOD FOR PREPARING MICROCARRIERS, MICROCARRIERS, AND APPLICATION THEREOF

(71) Applicant: FUJIFILM Corporation, Tokyo (JP)

(72) Inventor: Carolina Antonia Francina Maria Van Spreuwel-Goossens, Tilburg (NL)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/356,253

(22) Filed: Mar. 18, 2019

(65) Prior Publication Data

US 2019/0201536 A1  Jul. 4, 2019

Related U.S. Application Data

(60) Division of application No. 15/493,903, filed on Apr. 21, 2017, now Pat. No. 10,279,043, which is a continuation of application No. PCT/JP2015/079787, filed on Oct. 22, 2015.

(30) Foreign Application Priority Data

Oct. 22, 2014 (GB) .................................. 1418787.6
Oct. 22, 2014 (GB) .................................. 1418789.2

(51) Int. Cl.
*A61K 47/42* (2017.01)
*A61L 27/22* (2006.01)
*A61L 27/38* (2006.01)
*A61L 27/50* (2006.01)
*A61L 27/56* (2006.01)
*A61K 9/00* (2006.01)
*A61K 35/12* (2015.01)

(52) U.S. Cl.
CPC ............ *A61K 47/42* (2013.01); *A61K 9/0019* (2013.01); *A61K 35/12* (2013.01); *A61L 27/222* (2013.01); *A61L 27/38* (2013.01); *A61L 27/50* (2013.01); *A61L 27/56* (2013.01); *A61L 2400/06* (2013.01)

(58) Field of Classification Search
None
See application file for complete search history.

(56) References Cited

FOREIGN PATENT DOCUMENTS

| JP | 2009-520501 A | 5/2009 |
| KR | 10-2014-0063964 A | 5/2014 |
| WO | WO 03/104313 A1 | 12/2003 |

OTHER PUBLICATIONS

English translation of the Written Opinion of the International Searching Authority (PCT/ISA/237), issued in PCT/JP2015/079787, dated Jan. 12, 2016.
Extended European Search Report, dated Nov. 20, 2017, for corresponding European Application No. 15853265.5.
International Preliminary Report on Patentability for PCT/JP2015/079787, dated Apr. 25, 2017 (Form PCT/IB/373).
International Search Report (PCT/ISA/210), issued in PCT/JP2015/079787, dated Jan. 12, 2016.
Japanese Office Action, dated Feb. 6, 2018 for corresponding Japanese Application No. 2016-555275 with an English machine translation.
Non-Final Office Action dated Aug. 31, 2018 in copending U.S. Appl. No. 15/493,903.
Non-Final Office Action dated May 3, 2018 in copending U.S. Appl. No. 15/493,903.
Notice of Allowance dated Dec. 20, 2018 in copending U.S. Appl. No. 15/493,903.
Partial Supplementary European Search Report dated Sep. 25, 2017 issued in corresponding European Patent Application No. 15853265.5.
Pettersson et al., "Cell Expansion of Human Articular Chondrocytes on Macroporous Gelatine Scaffolds—Impact of Microcarrier Selection on Cell Proliferation," Biomedical Materials, vol. 6, No. 6, Sep. 29, 2011, pp. 1-13 (Total 14 pages), XP009165008.
Sofia Pettersson et al.; Cell expansion of human articular chondrocytes on macroporous gelatine scaffolds—impact of microcarrier selection on cell proliferation; Biomedical Materials, Institute of Physics; vol. 6, No. 6, Dec. 1, 2011; pp. 65001-1.
Written Opinion of the International Searching Authority (PCT/ISA/237), issued in PCT/JP2015/079787, dated Jan. 12, 2016.

*Primary Examiner* — Suzanne M Noakes
(74) *Attorney, Agent, or Firm* — Birch, Stewart, Kolasch & Birch, LLP (57) ABSTRACT

Objects of the present invention are to provide a preparation method which makes it possible to obtain porous microcarriers having unique properties and a unique particle size distribution and to provide porous gelatin microcarriers having excellent cell growth properties. According to the present invention, there are provided a method for preparing porous recombinant gelatin microcarriers that includes an emulsification step in which an emulsifier having a specific HLB value is used in a specific amount, and provided porous gelatin microcarriers having specific voids.

16 Claims, 3 Drawing Sheets

Specification includes a Sequence Listing.

SEQUENCE LISTING

```
<160> NUMBER OF SEQ ID NOS: 1

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175
```

```
Asp Gly Ala Pro Gly Lys Asp Gly Val Arg Gly Leu Ala Gly Pro Pro
            180                 185                 190
Gly Ala Pro Gly Leu Gln Gly Ala Pro Gly Leu Gln Gly Met Pro Gly
            195                 200                 205
Glu Arg Gly Ala Ala Gly Leu Pro Gly Pro Lys Gly Glu Arg Gly Asp
            210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
            245                 250                 255
Glu Arg Gly Asp Ala Gly Pro Lys Gly Ala Asp Gly Ala Pro Gly Lys
            260                 265                 270
Asp Gly Val Arg Gly Leu Ala Gly Pro Ile Gly Pro Pro Gly Glu Arg
            275                 280                 285
Gly Ala Ala Gly Leu Pro Gly Pro Lys Gly Glu Arg Gly Asp Ala Gly
            290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
            325                 330                 335
Gly Leu Gln Gly Met Pro Gly Glu Arg Gly Ala Ala Gly Leu Pro Gly
            340                 345                 350
Pro Lys Gly Glu Arg Gly Asp Ala Gly Pro Lys Gly Ala Asp Gly Ala
            355                 360                 365
Pro Gly Lys Asp Gly Val Arg Gly Leu Ala Gly Pro Pro Gly Ala Pro
            370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
            405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Pro Lys Gly Glu Arg Gly
            435                 440                 445
Asp Ala Gly Pro Lys Gly Ala Asp Gly Ala Pro Gly Lys Asp Gly Val
            450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
            485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
            515                 520                 525
Gly Met Pro Gly Glu Arg Gly Ala Ala Gly Leu Pro Gly Pro Lys Gly
            530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
            565                 570
```

METHOD FOR PREPARING MICROCARRIERS, MICROCARRIERS, AND APPLICATION THEREOF

CROSS-REFERENCE TO RELATED APPLICATIONS

The present application is a divisional of copending application Ser. No. 15/493,903 filed on Apr. 21, 2017, which is a continuation of PCT/JP2015/79787 filed on Oct. 22, 2015 and claims priorities under 35 U.S.C. § 119 of GB Patent Application No. 1418787.6 filed on Oct. 22, 2014 and GB Patent Application No. 1418789.2 filed on Oct. 22, 2014.

BACKGROUND OF THE INVENTION

1. Field of the Invention

The present invention relates to porous gelatin microcarriers, a method for preparing porous recombinant gelatin microcarriers, and the use of porous microcarriers.

2. Description of the Related Art

In a case where the body of a human being or animal is damaged, if it is a minor tissue damage, generally, the tissue can be repaired by the repair system the human being or animal originally has. However, in many cases, the damages such as cardiac infarction or injuries accompanying serious tissue damage cannot be repaired by the regenerative capacity intrinsic to the human being or the animal. In a case of serious tissue damage, a procedure assisting the tissue repair is necessary.

One of the problems resulting from extensive tissue damage is how the formed space or hole will be closed or filled. As a solution to this problem, it is possible to use a scaffold as a (semi)permanent filler for filling up the space or hole of the site where the tissue is lossed. The scaffold can also be used as a slow-release reservoir for releasing a growth factor or a medicine or for delivering cells. By seeding desired cells in the scaffold in advance before the cells are injected or transplanted into the body, cell delivery can be performed.

Gelatin is used in some cases as a material constituting the scaffold in the form of a porous microcarrier or the like. Therefore, products of porous gelatin microcarriers are drawing attention.

In WO03/104313, Nilsson suggests a method for preparing a porous natural gelatin microcarrier which can be used as scaffolds for tissue regeneration. The Nilsson's preparation method includes two-stage emulsification steps. In each of the steps, a surfactant having a specific HLB value (hydrophilic balance) is used. According to Nilsson, in the first emulsification step, a homogeneous water-soluble gelatin solution containing an emulsifier having a HLB value of greater than 9 is prepared, and a first composition containing an organic solvent and an emulsifier having a HLB value of greater than 9 is added thereto. Furthermore, according to Nilsson, in the second emulsification step, a second composition containing an organic solvent and an emulsifier having a HLB value of less than 8 is added, and finally a gelatin material is cooled and coagulates, thereby obtaining microcarriers.

SUMMARY OF THE INVENTION

Through the study of the inventors of the present invention, the present researchers tried to prepare porous microcarriers from recombinant gelatin based on the method of Nilsson et al., using natural gelatin. However, when the Nilsson's method was used for the recombinant gelatin, paste-like particles or lumps of nonhomogeneous particles were obtained, and none of these were ideal for cell culture. Therefore, the present invention aims to provide a preparation method which makes it possible to obtain porous microcarriers which have unique properties and a unique particle size distribution.

Furthermore, through the study of the inventors of the present invention, the present researchers tried to prepare porous microcarriers having ameliorated cell growth characteristics. The present invention also aims to provide porous gelatin microcarriers having excellent cell growth characteristics.

As a result of intensive investigation, the inventors of the present invention found that, surprisingly, by changing the method of Nilsson et al., and performing the second emulsification step by using a non-water-soluble liquid that substantially does not contain or does not contain at all the emulsifier having HLB of less than 8, porous recombinant gelatin microcarriers having excellent cell growth characteristics can be obtained. What the inventors found is knowledge that is completely opposite to the Nilsson's method in which the emulsifier is used in a significant amount in the second emulsification step. As will be specifically described below, the aforementioned change from the Nilsson's method can be used for recombinant gelatin so as to provide a previously unknown porous microcarriers having a unique properties and a unique particle size distribution.

The inventors of the present invention also found that, surprisingly, microcarriers having the characteristics defined as will be described later can be prepared by the aforementioned method or the like and have particularly excellent cell growth characteristics compared to the commercially available microparticles on the market.

[1] A method for preparing porous recombinant gelatin microcarriers, comprising (a) a step of generating a first emulsion by mixing a composition containing water, recombinant gelatin, a non-water-soluble liquid, and an emulsifier, (b) a step of generating a second emulsion by mixing the first emulsion with a non-water-soluble liquid at a temperature higher than a gelation temperature of gelatin, and (c) a step of cooling the second emulsion at a temperature at which gelatin coagulates, in which the non-water-soluble liquid used in the step (b) contains an emulsifier having a HLB value of less than 8 in an amount of less than 0.5% by weight.

[2] The method for preparing porous microcarriers according to [1], in which the non-water-soluble liquid used in the step (b) does not contain the emulsifier having a HLB value of less than 8.

[3] The method for preparing porous microcarriers according to [1], in which the non-water-soluble liquid used in the step (b) does not contain an emulsifier.

[4] The method for preparing porous microcarriers according to any one of [1] to [3], in which a HLB value of the emulsifier used in the step (a) is greater than 9.

[5] The method for preparing porous microcarriers according to any one of [1] to [4], in which a pH of the first emulsion is within a range of 3 to 11.

[6] The method for preparing porous microcarriers according to any one of [1] to [5], in which the recombinant gelatin has at least 5 isoelectric points.

[7] The method for preparing porous microcarriers according to any one of [1] to [6], in which the recombinant gelatin does not contain hydroxyproline.

[8] The method for preparing porous microcarriers according to any one of [1] to [7], further comprising (d) a step of removing coagulated gelatin from the second emulsion.

[9] The method for preparing porous microcarriers according to any one of [1] to [8], in which the recombinant gelatin contains at least 3 RGD motifs.

[10] The method for preparing porous microcarriers according to any one of [1] to [9], in which the recombinant gelatin contains at least two lysine residues, the two lysine residues are extreme lysine residues, a first extreme lysine residue is a lysine residue closest to an N-terminal of the gelatin, a second extreme lysine residue is a lysine residue closest to a C-terminal of the gelatin, and the extreme lysine residues are separated from each other by at least 25% of a total number of amino acid residues in the gelatin.

[11] The method for preparing porous microcarriers according to any one of [1] to [10], in which in the step (b), a volume of the non-water-soluble liquid is greater than a volume of the first emulsion.

[12] The method for preparing porous microcarriers according to any one of [1] to [11], in which in the step (c), the cooling is performed at 0.1° C. to 20° C./min.

[13] The method for preparing porous microcarriers according to any one of [1] to [12], in which the first emulsion contains the recombinant gelatin in an amount of at least 1% to 15% by weight.

[14] The method for preparing porous microcarriers according to any one of [1] to [13], in which the composition used in the step (a) contains the recombinant gelatin in an amount of 1 to 15% by weight, water in an amount of 10 to 70% by weight, the non-water-soluble liquid in an amount of 20 to 90% by weight, and the emulsifier in an amount of 0.5 to 20% by weight.

[15] The method for preparing porous microcarriers according to any one of [1] to [14], further comprising a step of cross-linking the gelatin in the step (b) and/or after the step (b).

[16] The method for preparing porous microcarriers according to any one of [1] to [15], further comprising a step of performing thermal dehydration cross-linking on the gelatin after the step (b).

[17] Porous recombinant gelatin microcarriers obtained by the method for preparing porous microcarriers according to any one of [1] to [16].

[18] The porous recombinant gelatin microcarriers according to [17] that have surface pores having a mean diameter of at least 5 μm and have a mean void volume of at least 50% by volume.

[19] The porous recombinant gelatin microcarriers according to [17] or [18] that have a mean particle size of 20 to 800 μm.

[20] The porous recombinant gelatin microcarriers according to any one of [17] to [19] that have a mean density of 0.04 to 0.5 g/cm$^3$.

[21] The porous recombinant gelatin microcarriers according to any one of [17] to [20] that have a mean volume of 2 to 25 cm$^3$/g.

[22] The porous recombinant gelatin microcarriers according to any one of [18] to [21] that are obtained by the method for preparing porous microcarriers according to any one of [1] to [16].

[23] The porous recombinant gelatin microcarriers according to [17] that have a mean particle size of 20 to 800 in which at least 80% of the microcarriers have a particle size that is 30% to 200% of the mean particle size.

[24] A use of the porous recombinant gelatin microcarriers according to any one of [17] to [23] as cell carriers.

[25] A use of the porous recombinant gelatin microcarriers according to any one of [17] to [23] as scaffolds for tissue damage repair.

[26] A composite material comprising the porous recombinant gelatin microcarriers according to any one of [17] to [23] and cells, in which the cells exist on a surface and/or on the inside of the microcarriers.

[27] A composition for injection comprising a pharmacologically acceptable carrier and the porous recombinant gelatin microcarriers according to any one of [17] to [23] or the composite material according to [26].

[28] The composition for injection according to [27] that can be injected through a syringe having an internal caliber of 80 to 4,000 μm.

[29] Porous gelatin microcarriers having voids, in which at least half of the voids are spherical and/or at least half of the voids have a diameter that is −30% to +30% of a mean diameter of the voids.

[30] The microcarriers according to [29] that have surface pores having a mean diameter of at least 5 μm.

[31] The microcarriers according to [29] or [30] that have at a mean void volume of at least 50% by volume.

[32] The microcarriers according to any one of [29] to [31], in which the mean diameter of the voids is within a range of 5% to 25% of a mean particle size of the microcarriers.

[33] The microcarriers according to any one of [29] to [32] that have a mean particle size of 20 to 800 μm.

[34] The microcarriers according to any one of [29] to [33] that have a mean density of 0.04 to 0.5 g/cm$^3$.

[35] The microcarriers according to any one of [29] to [34] that have a mean volume of 2 to 25 cm$^3$/g.

[36] The microcarriers according to any one of [29] to [35] that have a mean particle size of 20 to 800 μm, in which at least 80% of the microcarriers have a particle size that is 30% to 200% of the mean particle size.

[37] The microcarriers according to [29] that have surface pores having a mean diameter of at least 5 μm, a mean void volume of at least 50% by volume, and at a mean particle size of 20 to 800 μm, in which at least half or more of the voids are spherical, at least 80% of the microcarriers have a particle size that is 30% to 200% of the mean particle size, and a mean diameter of the voids is within a range of 5% to 25% of the mean particle size of the microcarriers.

[38] The microcarriers according to [29] that have surface pores having a mean diameter of at least 5 μm, a mean void volume of at least 50% by volume, and a mean particle size of 20 to 800 μm, in which at least half or more of the voids have a diameter that is −30% to +30% of a mean diameter of the voids, at least 80% of the microcarriers have a particle size that is 30% to 200% of the mean particle size of the microcarriers, and the mean diameter of the voids is within a range of 5% to 25% of the mean particle size of the microcarriers.

[39] The microcarriers according to [37] or [38], in which at least 75% of the voids are spherical.

[40] The microcarriers according to any one of [29] to [39], in which the gelatin is recombinant gelatin.

[41] The microcarriers according to any one of [29] to [40], in which the gelatin is recombinant gelatin having at least 5 isoelectric points.

[42] The microcarriers according to any one of [29] to [41], in which the gelatin is recombinant gelatin which does not contain hydroxyproline.

[43] The microcarriers according to any one of [29] to [42], in which the gelatin is recombinant gelatin containing at least 3 RGD motifs.

[44] The microcarriers according to any one of [29] to [43], in which the gelatin is recombinant gelatin that contains at least two lysine residues, the two lysine residues are extreme lysine residues, a first extreme lysine residue is a lysine residue closest to an N-terminal of the gelatin, a second extreme lysine residue is a lysine residue closest to a C-terminal of the gelatin, and the extreme lysine residues are separated from each other by at least 25% of a total number of amino acid residues in the gelatin.

[45] A use of the microcarriers according to any one of [29] to [44] as cell carriers. [46] A use of the microcarriers according to any one of [29] to [44] as scaffolds for tissue damage repair.

[47] A composite material comprising the microcarriers according to any one of [29] to [44] and cells, in which the cells exist on a surface and/or on the inside of the microcarriers.

[48] A composition for injection, comprising a pharmacologically acceptable carrier and the microcarriers according to any one of [29] to [44] or the composite material according to [47].

[49] The composition for injection according to [47] that can be injected through a syringe having an internal caliber of 80 to 4,000 μm.

By the method for preparing porous recombinant gelatin microcarriers of the present invention, as will be specifically described later, it is possible to provide previously unknown porous microcarriers having a unique properties and a unique particle size distribution for recombinant gelatin.

Furthermore, the porous gelatin microcarriers of the present invention have particularly excellent cell growth characteristics compared to commercially available microparticles on the market.

Figure 1A:
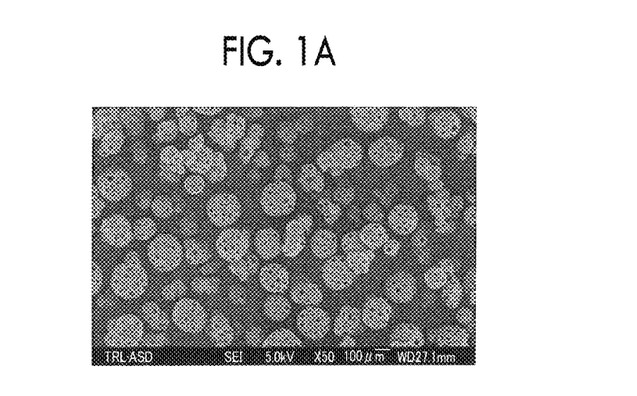
FIGS. 1A to 1C are scanning electron microscope (SEM) images of microcarriers obtained by a method of the present invention, in which the non-water-soluble liquid used in the step (b) contains an emulsifier having a HLB value of less than 8 in an amount of less than 0.5% by weight.
Figure 1B:
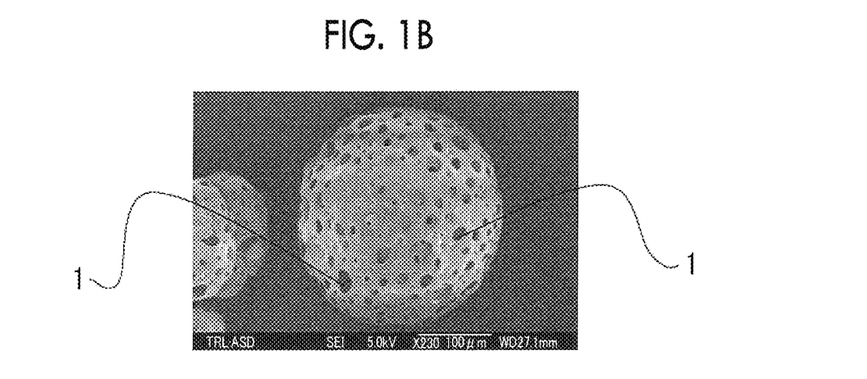
Figure 1C:
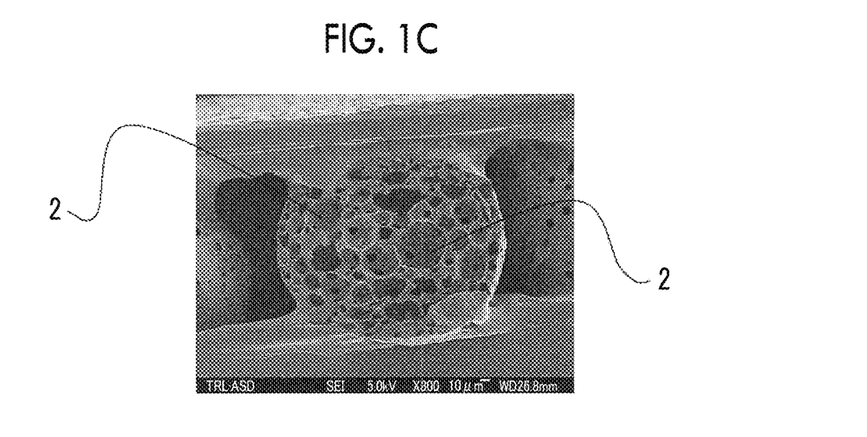

FIG. 1A is an image magnified by a factor of 50 that schematically shows microcarriers obtained by the method of the present invention. The microcarriers of FIG. 1A have an excellently spherical shape and a narrow range of size distribution, and practically do not form or do not form at all a lump which is an aggregate of particles. FIG. 1B is an image magnified by a high factor of 230 that shows microcarriers obtained by the method of the present invention. In FIG. 1B, surface pores (1) can be clearly observed. The surface pores (1) are linked to voids in the microparticles (the internal voids cannot be seen in the image). FIG. 1C is a cross-sectional view of microcarriers obtained by the method of the present invention. FIG. 1C shows the internal voids (2), at least half of the voids are spherical and have a diameter that is −30% to +30% of a mean diameter of the voids. FIGS. 2C and 3C, which are cross-sectional view of microcarriers of comparative examples and correspond to FIG. 1C, show that the internal voids are large. The voids (2) of FIG. 1C are practically spherical. In a case where the spherical cavities overlap or contact each other, a void binding to a neighboring void has small pores on the wall thereof. In the relationship between the voids (2) and the microcarriers in terms of size, most of the voids (2) are large and have a narrow range of size distribution (for example, the voids (2) substantially have the same size).

The microcarriers of the present invention enable cell culture accompanying excellent cell growth from the viewpoint of the amount and proportion of cells. Particularly, the microcarriers can be suitably used for dynamic cell culture in which the microcarriers for culture are kept suspended, and handling of the microcarriers is easy.

Figure 2A:
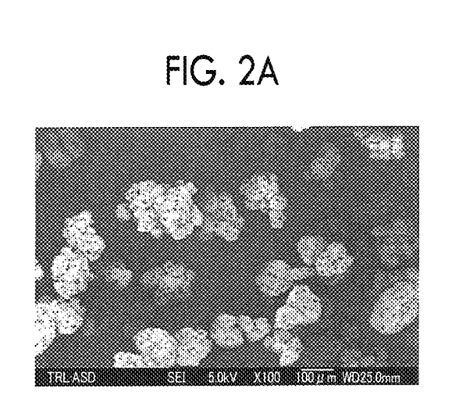
FIGS. 2A to 2C are SEM images of microcarriers of comparative examples that are obtained by modifying the method of the present invention, in which the non-water-soluble liquid used in the step (b) contains an emulsifier having a HLB value of less than 8 in an amount of equal to or greater than 0.5% by weight.
Figure 2B:
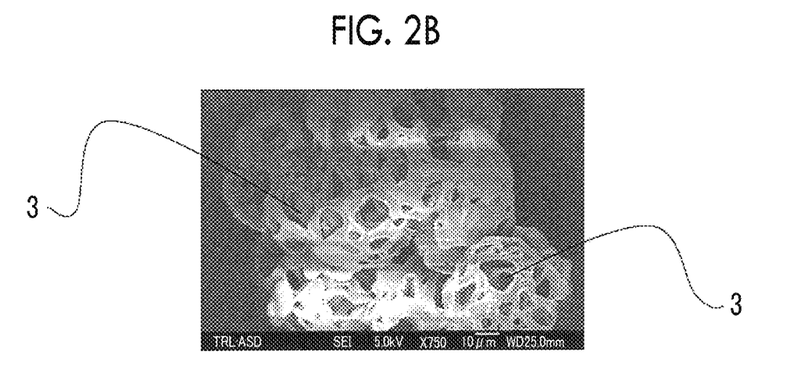
Figure 2C:
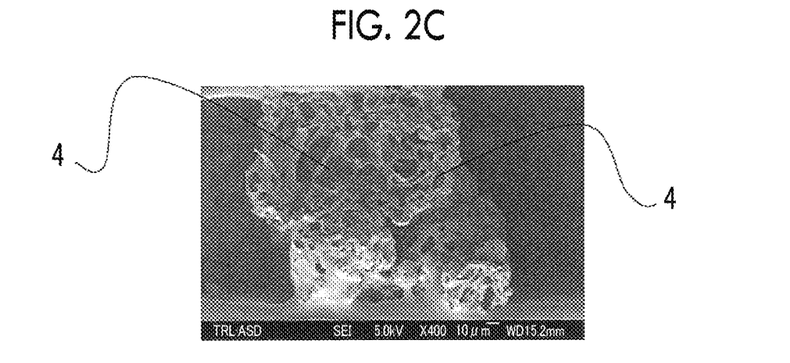

FIG. 2A is an image magnified by a factor of 100 that schematically shows the microcarriers obtained by the method of the comparative examples described above. As will be specifically described in the section of example, the microcarriers of the comparative examples are obtained by a different method in which corn oil of the step (b) contains an emulsifier having a HLB value of less than 8 in an amount of 5% by weight. Most of the microcarriers in FIG. 2A are lumped together. As a result, the microcarriers form secondary particles having non-uniform shapes and have a wide range of size distribution. FIG. 2B is an image magnified by a factor of 750 and shows the microcarriers obtained by the method of a comparative example. The microcarriers of the comparative example are non-spherical, and have large surface pores (3). The microcarriers are lumped together, and form a secondary structure. FIG. 2C is a cross-sectional view of the microcarriers obtained by the method of the comparative example. As is evident from FIG. 2C, from the viewpoint of the size and shape of internal voids (4), the microcarriers are irregular, and the diameter of most of the microcarriers is smaller than the diameter of the microcarriers of the present invention shown in FIG. 1B. The voids (4) in the microparticles of FIG. 2C have a very wide range of size distribution. Most of the voids (4) of FIG. 2C are not spherical, and less than half of the voids have a diameter that is −30% to +30% of the mean diameter of the voids.

Figure 3A:
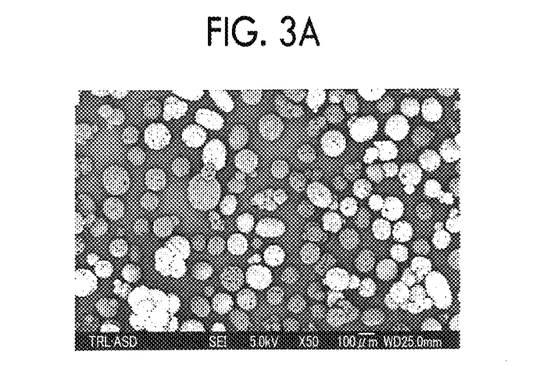
FIGS. 3A to 3C are SEM images of CultiSpher G (registered trademark) microcarriers commercially available from GE Healthcare Life Sciences.
Figure 3B:
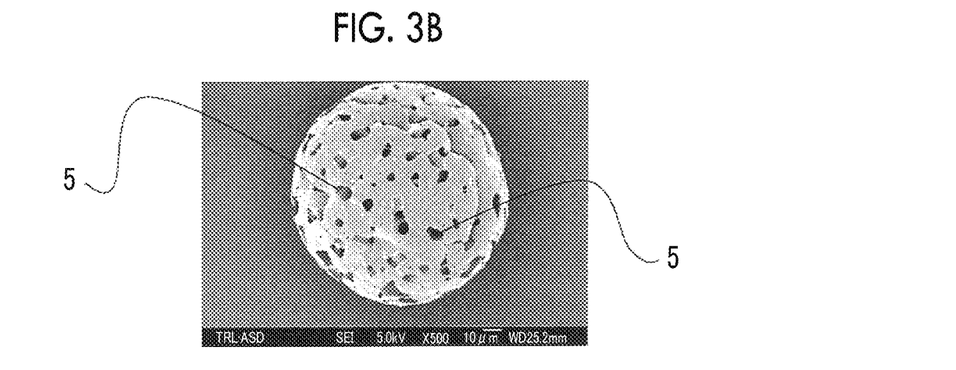
Figure 3C:
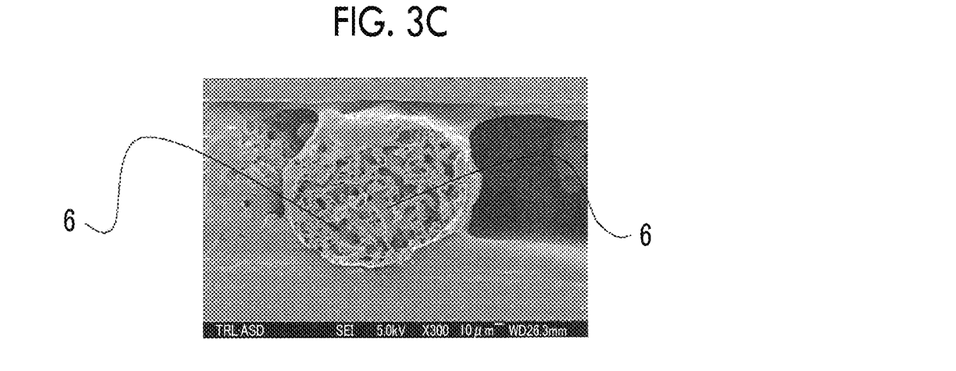

FIG. 3A is an image magnified by a factor of 50 and schematically shows commercially available microcarriers CultiSpher G (registered trademark). FIG. 3B is an image magnified by a factor of 600 and shows a single microcarrier CultiSpher G (registered trademark). In this image, surface pores (5) can be clearly observed. FIG. 3C is an image magnified by a factor of 300 and shows a cross-section of CultiSpher G (registered trademark). Compared to the voids in FIG. 1C, the voids (6) in the microcarriers CultiSpher G (registered trademark) shown in FIG. 3C have irregular sizes and shapes, and most of them are not spherical voids but rather cylindrical or tubular pores. Many of the voids (6) shown in FIG. 3C have a size smaller than the particle size of the microcarriers, and have a wider range of size distribution compared to the microcarriers of FIG. 1C. Most of the voids (6) of FIG. 3C are not spherical, and less than half of the voids have a diameter that is −30% to +30% of the average diameter of the voids.

DESCRIPTION OF THE PREFERRED EMBODIMENTS

The term "recombinant gelatin" used in the present specification includes recombinant collagen, and the term "gelatin" includes collagen. Accordingly, in the present specification, the terms "gelatin", "collagen", "collagen polypeptide", and "gelatin polypeptide" are used in the same sense.

The voids will be described as spaces or cavities in some cases.

The average molecular weight of the recombinant gelatin according to the present invention is preferably less than 150 kDa, and more preferably less than 100 kDa. The average molecular weight is preferably at least 5 kDa, more preferably at least 10 kDa, and even more preferably at least 30 kDa. The average molecular weight of the recombinant gelatin is preferably within a range of 50 kDa to 100 kDa, 20 kDa to 75 kDa, and 5 kDa to 40 kDa. When high-mass concentration gelatin is required for low viscosity, the molecular weight is preferably lower than the above. The gelatin of the porous gelatin microcarriers of the present invention is not limited to recombinant gelatin. However, the preferred range of the average molecular weight of the gelatin is the same as the range described above regarding the aforementioned recombinant gelatin.

The gelatin according to the present invention is preferably recombinant gelatin.

The recombinant gelatin is commercially available, and for example, those manufactured by FUJIFILM Corporation can be obtained. The recombinant gelatin can be prepared by a known method. For example, the methods described in EP0926543 and EP1014176 can be used. The contents of the methods are incorporated into the present specification by reference. The technique of preparing recombinant gelatin is also described in "High yield secretion of recombinant gelatins by Pichia patoris, M. W. T. Werten et al. Yeast 15, 1087-1096 (1999)". WO2004/85473 also describes suitable recombinant gelatin.

It is possible to exemplify an embodiment in which the recombinant gelatin contains at least two lysine residues, the two lysine residues are extreme lysine residues, a first extreme lysine residue is a lysine residue closest to an N-terminal of the gelatin, a second extreme lysine residue is a lysine residue closest to a C-terminal of the gelatin, and the extreme lysine residues are separated from each other by at least 25% of a total number of amino acid residues in the gelatin. This recombinant gelatin can be obtained by, for example, the method described in US2009/0246282.

As another embodiment of the present invention, it is possible to exemplify an embodiment in which the recombinant gelatin contains at least two amino acid residues, the two amino acid residues are extreme amino acid residues, the amino acid residues are each independently selected from an aspartic acid residue and a glutamic acid residue, a first extreme aspartic acid residue or glutamic acid residue is an aspartic acid residue or glutamic acid residue closest to an N-terminal of a polypeptide, a second aspartic acid residue or glutamic acid residue is an aspartic acid residue or glutamic acid residue closest to a C-terminal of a polypeptide, and either or both of the extreme aspartic acid residue and glutamic acid residue are separated from each other by at least 25% of a total number of amino acid residues in a recombinant gelatin polypeptide. In the aforementioned another embodiment of the present invention, the recombinant gelatin has at least one aspartic acid residue or glutamic acid residue between the extreme aspartic acid residues and/or between the extreme glutamic acid residues.

In an embodiment, the polypeptide of the recombinant gelatin does not form a stable triple helix particularly not at a temperature of higher than 5° C. or at a temperature of higher than 25° C.

The recombinant gelatin according to the present invention preferably contains proline in a GXY triplet corresponding to gelatin derived from mammals or homothermal animals such as fishes.

In order to prevent the formation of a stable triplet helix, the proportion of a hydroxyl group-containing amino acid in the amino acids in the recombinant gelatin is preferably less than 2% and more preferably less than 1%. The existence of hydroxyproline can be prevented by expressing it in a microorganism that does not coexpress an enzyme causing hydroxylation of a proline residue or by satisfying the action thereof by another method. "Substantially 0" means that the existence of hydroxyproline in the growth medium such as yeast causes some of the amino acids to be incorporated into the gelatin.

In a suitable embodiment, the recombinant gelatin has excellent cell adhesion characteristics and preferably does not have any of health-related risks. Such an embodiment can be achieved by using RGD-enriched recombinant gelatin, for example, recombinant gelatin in which a ratio of RGD motifs to the total number of amino acids is at least 0.4. In a case where the RGD-enriched gelatin has 350 or more amino acids, it is preferable that at least one RGD motif is contained in each range of the 350 amino acids. The ratio of the RGD motif is preferably at least 0.6, more preferably at least 0.8, even more preferably at least 1.0, still more preferably at least 1.2, and most preferably at least 1.5.

A ratio of 0.4 of the RGD motif corresponds to a state where a single RGD sequence emerges in each stretch of 250 amino acids. The number of RGD motifs is an integer. Therefore, in order for the ratio of the RGD motif to be 0.4%, the gelatin containing 251 amino acids must have at least two RGD sequences. The RGD-enriched recombinant gelatin preferably has at least two RGD motifs in each stretch of 250 amino acids, more preferably has at least 3 RGD motifs in each stretch of 250 amino acids, and most preferably has at least 4 RGD motifs in each stretch of 250 amino acids. In another embodiment, the RGD-enriched gelatin has at least 4 RGD motifs, preferably has at least 6 RGD motifs, more preferably has at least 8 RGD motifs, and most preferably has 12 to 16 RGD motifs.

The recombinant gelatin according to the present invention is preferably derived from a collagen sequence. The nucleic acids encoding collagen are generally described in known documents (for example, refer to Fuller and Boedtker (1981) Biochemistry 20: 996-1006; Sandell et al. (1984) J Biol Chem 259: 7826-34; Kohno et al. (1984) J Biol Chem 259: 13668-13673; French et al. (1985) Gene 39: 311-312; Metsaranta et al. (1991) J Biol Chem 266: 16862-16869; Metsaranta et al. (1991) Biochim Biophys Acta 1089: 241-243; Wood et al. (1987) Gene 61: 225-230; Glumoff et al. (1994) Biochim Biophys Acta 1217: 41-48; Shirai et al. (1998) Matrix Biology 17: 85-88; Tromp et al. (1988) Biochem J 253: 919-912; Kuivaniemi et al. (1988) Biochem J 252: 633640; and Ala-Kokko et al. (1989) Biochem J 260: 509-516).

The RGD motif-enriched recombinant gelatin can be prepared by a general method described in, for example, US2006/0241032.

For being used as a medication or used for medical purpose, the recombinant gelatin is preferable which has an amino acid sequence that is close to or the same as the amino acid sequence of the natural human collagen. The amino acid sequence of the gelatin is more preferably a repeating amino acid sequence in the natural human collagen, and particularly, the gelatin having an RGD motif-containing sequence for making RGD-enriched recombinant gelatin.

The ratio of the RGD motif in a selected sequence depends on the selected length of the selected sequence. If a shorter sequence is selected, the ratio of the RGD motif of the final recombinant gelatin inevitably becomes high. The repetition of the selected amino acid sequence can be used for providing recombinant gelatin having a molecular weight higher than that of the natural gelatin. Furthermore, it is possible obtain the RGD-enriched recombinant gelatin that is non-antigenic unlike the natural gelatin.

Accordingly, in a suitable embodiment, the recombinant gelatin includes a portion of the sequence of the natural human collagen. The gelatin is preferably RGD-enriched gelatin containing one or more sites of the amino acid sequence of one or more amino acid sequences of natural human gelatin, in a proportion of equal to or higher than 80%. Each of the aforementioned sites of the sequence of the human gelatin preferably has a length consisting of at least 30 amino acids, more preferably has a length consisting of at least 45 amino acids, and even more preferably has a length consisting of at least 60 amino acids. For example, each of the sites has a length consisting of up to 240 amino acids, preferably has a length consisting of up to 150 amino acids, and more preferably has a length consisting of up to 120 amino acids. It is preferable that each of the sites includes one or more RGD sequences. The RGD-enriched gelatin preferably includes one or more sites of one or more sequences of the natural human collagen.

Examples of a suitable source of the recombinant gelatin used in the method of the present invention includes human COL1A1-1. The site of 250 amino acids including the RGD sequence is described in WO04/85473. The RGD sequence of the recombinant gelatin can bind to a specific receptor called integrin on a cell surface.

The RGD-enriched gelatin can be manufactured by the gene recombination methods described in EP-A-0926543, EP-A-1014176, or WO01/34646, and particularly by the methods described in examples of EP-A-0926543 and EP-A-1014176. A preferred method for manufacturing the RGD-enriched recombinant gelatin includes a step of initiating the method by using a natural nucleic acid sequence encoding a portion of a collagen protein including an RGD amino acid sequence. By repeating the sequence, RGD-enriched recombinant gelatin can be obtained.

In this way, the recombinant gelatin can be manufactured by expressing a nucleic acid encoding gelatin in an appropriate microorganism. This method can be appropriately performed using fungal cells or yeast cells. As a host cell, high-expressing host cells such as Hansenula, Trichoderma, Aspergillus, Penicillium, Saccharomyces, Kluyveromyces, Neurospora, or Pichia are suitable. The fungal cells and yeast cells are more preferable than bacteria because the cells are not easily affected by the inappropriate expression of a repeating sequence. It is more preferable that the host does not have a high level of protease that hinders the expression of a gelatin structure. In this respect, Pichia or Hansenula can be exemplified as an extremely suitable expression system. The use of Pichia pastoris as an expression system is disclosed in EP0926543 and EP1014176. A microorganism can prevent the activation of a post-translational processing mechanism such as proline hydroxylation or lysine hydroxylation. In contrast, the host system can have intrinsic proline hydroxylation activity by hydroxylating gelatin with high efficiency.

In another embodiment, the recombinant gelatin has, compared to the natural gelatin, a higher glass transition temperature (Tg) which is, for example, equal to or higher than 170° C. and particularly equal to or higher than 180° C.

The recombinant gelatin having a higher Tg compared to the natural gelatin is described in WO05/11740.

In another embodiment, a degree of glycosylation of the recombinant gelatin is lower than that of the natural gelatin. For example, the degree of glycosylation of the recombinant gelatin is less than 2% by weight, preferably less than 1% by weight, more preferably less than 0.5% by weight, even more preferably less than 0.2% by weight, and still more preferably less than 0.1% by weight. In a preferred embodiment, the recombinant gelatin does not undergo glycosylation. The degree of glycosylation represented by % by weight means the total weight of carbohydrate per unit weight of the gelatin, and can be determined by Matrix Assisted Laser Desorption Ionization mass spectrometry (MALDI-TOF-MS) or by a Dubois' titration method. The term "glycosylation" means not only the glycosylation involved in monosaccharide but also the glycosylation involved in polysaccharide such as di-, tri-, and tetrasaccharide.

There are various methods for reducing or preventing glycosylation. The glycosylation is post-translational modification, and due to the glycosylation, a covalent bond is formed between carbohydrate and a certain amino acid of the gelatin. The amino acid sequence and the host cell (and an enzyme, particularly, glycosyltransferase) determine the degree of glycosylation. There are two kinds of glycosylation including N-glycosylation which begins when N-acetylglucosamine (GlcNAc) binds to an amide group of asparagine (N or Asn) and O-glycosylation in which GalNAc generally binds to an amino acid serine (S or Ser) or threonine (T or Thr).

Therefore, by selecting an appropriate host cell and/or by modifying or selecting a sequence without a consensus site recognized by glycosyltransferase of the host, it is possible to control, particularly reduce, or prevent the glycosylation. The chemical synthesis of gelatin can be used for preparing gelatin which does not undergo glycosylation. By using a known method, recombinant gelatin that undergoes glycosylation can be generated, and then the entirety or most of carbohydrate thereof can be removed. Alternatively, the gelatin that has not undergone glycosylation can be separated from the gelatin having undergone glycosylation.

In another preferred embodiment, the recombinant gelatin contains hydroxyproline as an amino acid residue in a proportion of less than 10% and preferably in a proportion of less than 5%. It is preferable that the recombinant gelatin does not contain a hydroxyproline residue. It is also preferable that the recombinant gelatin does not contain a hydroxylated amino acid residue.

In another embodiment, the recombinant gelatin has at least 5 isoelectric points. For example, the recombinant gelatin has 5 to 11 isoelectric points, more preferably has 6 or more isoelectric points, and even more preferably has 7 or more isoelectric points, such that recombinant gelatin having a net positive charge is provided under physiological conditions. While not wishing to be bounded by theory, it is considered that the positive charge assists the attractive force, the interaction, and the binding between cells having a membrane that is negatively charged overall.

In a case where the gelatin is recombinant gelatin, the porous gelatin microcarriers of the present invention can be prepared by the method for preparing porous recombinant gelatin microcarriers of the present invention.

The pH of the composition used in the step (a) is preferably within a range of 3 to 11, and more preferably within a range of 4 to 8. The pH of the second emulsion is preferably within a range of 3 to 11, and more preferably within a range of 4 to 8. It is preferable that the composition used in the step (a) contains an emulsifier having hydrophilic-lipophilic balance (HLB) which is preferably greater than 9, more preferably greater than 10, and particularly preferably 13 to 19. It is also possible to use two or more kinds of the emulsifier. Examples of suitable emulsifiers include PEG400 monooleic acid polyoxyethylene monooleic acid (HLB: 11.4), PEG400 monostearate polyoxyethylene monolaurate (HLB: 11.6), PEG400 monolaurate polyoxyethylene monolaurate (HLB: 13.1), potassium oleate (HLB: 20.0), sodium lauryl sulfate (HLB: 40), sodium oleate (HLB: 18), Myrj (registered trademark) 52 (polyoxyethylene stearate, HLB: 17), Brij (registered trademark) 58 (polyoxyethylene cetyl alcohol, HLB: 16), Tween (registered trademark) 20 (polyoxyethylene sorbitan lauric acid monoester, HLB: 16.7), Tween 21 (polyoxyethylene sorbitan lauric acid monoester, HLB: 13.3), Tween 40 (polyoxyethylene sorbitan monopalmitate, HLB: 15.6), Tween 60 (sorbitan polyoxyethylene monostearate, HLB: 14.9), Tween 61 (sorbitan polyoxyethylene monostearate, HLB: 9.6), Tween 65 (polyoxyethylene sorbitan tristearate, HLB: 10.5), Tween 80 (polyoxyethylene sorbitan oleic acid monoester, HLB: 15.0), Tween 81 (polyoxyethylene sorbitan oleic acid monoester, HLB: 10.0), and Tween 85 (polyoxyethylene sorbitan trioleate, HLB: 11.0). Among these, Tween 80, Tween 40, Myrj 52, Brij 58, and a combination of two or more of these are preferable.

The suitable non-water-soluble liquid used in the step (a) is alkyl acetate (for example, ethyl acetate), hydrocarbon (for example, hexane, heptane, cyclohexane, toluene, or xylene), halogenated hydrocarbon (for example, methylene chloride, monochlorobenzene, or dichlorobenzene), oil (for example, vegetable oil (for example, corn oil)), paraffin oil, industrial lubricating oil, and a combination of two or more of these. Among these, corn oil is particularly preferable as the non-water-soluble liquid.

The non-water-soluble liquid used in the step (b) preferably contains an emulsifier having a HLB value of less than 8 in an amount of less than 0.1% by weight, more preferably does not contain an emulsifier having a HLB value of less than 8, and even more preferably does not contain an emulsifier.

Examples of the emulsifier having a HLB value of less than 8 include glycerin monostearate (HLB: 3.8), Span (registered trademark) 40 (sorbitan monopalmitate, HLB: 6.7), Span 60 (sorbitan monostearate, HLB: 4.7), Span 65 (sorbitan tristearate, HLB: 2.1), Span 80 (sorbitan oleic acid monoester, HLB: 4.3), and Span 85 (sorbitan trioleate, HLB: 1.8).

The non-water-soluble liquid used in the step (b) may be the same as or different from the non-water-soluble liquid used in the step (a). In the step (a), a volume ratio of water to the non-water-soluble liquid is smaller than 1:1 and particularly preferably smaller than 1:2. In the step (b), a volume ratio of water to the non-water-soluble liquid is smaller than 2:1, and particularly preferably smaller than 1:1.

Generally, the first emulsion and the second emulsion each has two phases, that is, a non-water-soluble phase and a water phase. It is preferable that the step (a) is performed in a state where the volume of the non-water-soluble phase is the same as or greater than the volume of the water phase, for example, in a state where the volume of the non-water-soluble phase is twice or greater than the volume of the water phase. It is preferable that the step (b) is performed in a state where the volume of the non-water-soluble phase is greater than the volume of the first emulsion, for example, in a state where the volume of the non-water-soluble phase is not less than twice the volume of the first emulsion.

The method of the present invention can further include a step of cross-linking the gelatin, in the step (b) and/or after the step (b). The cross-linking is chemical cross-linking such as chemical cross-linking using a cross-linking agent and preferably thermal cross-linking such as thermal dehydration cross-linking. The gelatin can be cross-linked through, for example, an amine group of lysine, a carboxyl group of glutamic acid or aspartic acid, or a combination of these.

As a suitable cross-linking agent of the chemical cross-linking, a cross-linking agent is preferable which does not cause toxicity or antigenicity when being released during biodegradation. Examples of the suitable cross-linking agent include glutaraldehyde, water-soluble carbodiimide, a bisepoxy compound, formalin, 1-ethyl-3-(3-dimethylaminopropyl)carbodiimide, bis-hydroxy-succinimide, glycidyl ether (for example, alkylene glycol diglycidyl ether or polyglycerol polyglycidyl ether), diisocyanate (for example, hexamethylene diisocyanate), diphenyl phosphoryl azide, D-ribose, genepin, and a combination of these. The cross-linking method is also described in "Weadock et. Al. in Evaluation of collagen cross-linking techniques (Biomater. Med. Devices Artif. Organs, 1983-1984, 11 (4): 293-318"). Among the above, it is possible to suitably use water-soluble 1-ethyl-3-(3-dimethylaminopropyl)carbodiimide (EDC). Furthermore, hexamethylene diisocyanate can be suitably used. Examples of other suitable cross-linking agents include triazine such as dichlorohydroxytriazine. Examples of other cross-linking compounds include divinylsulfone, di-anhydride, bifunctional imidate, di-epoxy, and dimaleimidine. It is also possible to use a bifunctional cross-linking agent having different active substituents in a single compound, such as a bifunctional cross-linking compound containing epoxide and anhydride. An enzymatic cross-linking agent such as trans-glutaminase is also useful.

The cross-linking agent may have more than two functional groups, and examples thereof include cyanuric chloride (trifunctional group) and a compound containing two epoxide and anhydride. These cross-linking agents generally react with an amino group and/or a sulfhydril group existing in an amino acid of the gelatin. If necessary, more than one cross-linking agents can be used. The cross-linking is spontaneously initiated when the cross-linking agent contacts the gelatin, after the pH or the like is adjusted, by light, or through other activation mechanisms.

Glutaraldehyde is a particularly useful cross-linking agent, and this cross-links two lysine residues. EDC is another suitable biocompatible cross-linking agent, and this binds an amino group to a carboxyl group. Hexamethylene diisocyanate can also be used as a cross-linking agent. During the thermal dehydration cross-linking, cross-linking is induced due to the condensation of an amino group and a carboxyl group existing in the gelatin, and hence an amide bond is formed. The thermal dehydration cross-linking is preferably performed at a temperature of equal to or higher than 120° C.

In a case where the porous gelatin microcarriers of the present invention is gelatin other than recombinant gelatin, suitable embodiments relating to the cross-linking are the same as described above relating to the aforementioned cross-linking.

In order to make a contribution to the formation of particles, the gelatin and the recombinant gelatin according to the present invention preferably have at least two lysine residues. The gelatin and the recombinant gelatin according to the present invention preferably has at least 3 lysine residues or has at least 4, 5, 6, 7, 8, 9, 10, 11, or 12 lysine residues. In another embodiment, the gelatin and the recombinant gelatin according to the present invention preferably contains, in addition to the lysine residues, at least two amino acids selected from aspartic acid and glutamic acid. The gelatin and the recombinant gelatin according to the present invention more preferably contains at least 3 aspartic acid and glutamic acid residues or contains at least 4, 5, 6, 7, 8, 9, 10, 11, or 12 aspartic acid and glutamic acid residues.

In order to make a contribution to the three-dimensional network structure of the microcarriers, the gelatin and the recombinant gelatin according to the present invention preferably contain lysine, aspartic acid and/or glutamic acid dispersed in gelatin molecules. Therefore, in an embodiment, each stretch of 50 amino acid residues has at least one lysine residue, and preferably has at least two lysine residues. Alternatively, each stretch of 50 amino acid residues has at least one aspartic acid or glutamic acid residue and preferably has at least two aspartic acid or glutamic acid residues, or, each stretch of 50 amino acid residues preferably has at least one lysine residue and at least one aspartic acid or glutamic acid residue. Preferably, each stretch of 40 amino acid residues, and more preferably, each stretch of 25 amino acid residues preferably has at least one lysine residue and/or at least one aspartic acid or glutamic acid residue.

It is preferable that the gelatin and the recombinant gelatin according to the present invention each contains cross-linkable amino acid residues not being adjacent to each other. For example, the cross-linkable amino acid residues preferably separated by at least 5 non-cross-linkable amino acids, more preferably separated by at least 10 non-cross-linkable amino acids. The cross-linkable amino acid residue contains a primary amine group (in addition to a primary amine group generally used for forming an amide bond in a protein skeleton), —SH, and/or carboxylic acid (in addition to carboxylic acid generally used for forming an amide bond in a protein skeleton).

It is preferable that the recombinant gelatin contains lysine residues at a higher proportion (%) or in a larger number compared to the natural gelatin, particularly for the following cross-linking. Many of cross-linking agents bind to a lysine residue and/or N-terminal amine. Generally, in the natural gelatin, each stretch of 1,000 amino acids contains 25 to 27 lysine residues and 112 to 133 glutamic and aspartic acids. In the recombinant gelatin used in the present invention, for example, the number of lysine residues can be set to be the same as above or can be reduced and become about less than 20, 15, 10, or 5 for each stretch of 1,000 amino acids. If necessary, for example, the number of lysine residues can be set to be the same as above or can be increased and become about greater than 30, 40, or 50 for each stretch of 1,000 amino acids. For example, the number of glutamic acid or aspartic acid residues existing in the recombinant gelatin used in the present invention can be set to be the same as above or can be reduced and become about less than 100, 90, 80, 70, 60, 50, 40, 30, 20, 10, or 5 for each stretch of 1,000 amino acids. If necessary, for example, the number can be set to be the same as above or can be increased and become about greater than 150 for each stretch of 1,000 amino acids. If necessary, some or all of the glutmaine and asparagine residues existing in the recombinant gelatin can be deaminated such that they can be converted into aspartic acid and glutamic acid residues.

In an embodiment, through a step of bringing the gelatin or the recombinant gelatin according to the present invention into contact with a cross-linking agent in an amount of 0.02 to 1.0 mmol per 1 gram of the gelatin or the recombinant gelatin, the gelatin or the recombinant gelatin is cross-linked. For example, per 1 gram of the gelatin or the recombinant gelatin according to the present invention, it is possible to use a cross-linking agent in an amount of about 0.02, 0.05, 0.1, 0.25, 0.5, 0.6, 0.7, 0.8, 0.9, or 1.9 mmol.

In another embodiment, through a step of bringing the gelatin or the recombinant gelatin according to the present invention into contact with 0.5 to 5.0 mmol of cross-linking agent per 1 gram of the gelatin or the recombinant gelatin, the gelatin or the recombinant gelatin is cross-linked. For example, per 1 gram of the gelatin or the recombinant gelatin according to the present invention, it is possible to use a cross-linking agent in an amount of about 0.5, 0.6, 0.7, 0.8, 0.9, 1.0, 2.0, 3.0, or 4.0, and 5.0 mmol.

In this way, in order to determine or customize the physical characteristics of the microcarriers, it is possible to use the amount of the cross-linking agent to be used and the number of the cross-linkable amino acid residues. By increasing the number of the cross-linkable residues and/or by increasing the concentration of the cross-linking compound, it is possible to obtain strong microcarriers that is particularly useful for the purpose subjected to a mechanical stress. By decreasing the number of the cross-linkable amino acid residues and/or by decreasing the concentration of the cross-linking compound, it is possible to obtain easily deformed microcarriers suitable for injection or for being used as a medication.

Thermal cross-linking is preferable because this makes it possible to avoid the potential chemical contamination of the gelatin or the recombinant gelatin according to the present invention that is particularly desirable when the microcarriers are used as a medication.

A degree of cross-linking affects the time taken for the gelatin microcarriers to degrade in the body. Therefore, the degradation ratio of the microcarriers for being used as intended can be controlled. For example, the degradation ratio can be controlled when the microcarriers of the present invention not containing cells are used for being injected into a wrinkled portion in the cosmetic surgery. The cells around the microcarriers move to the microcarriers and form colonies. The microcarriers slowly degrade due to the surrounding enzyme (for example, matrix metalloproteinase), the cells having moved occupy the wrinkled portion, and as a result, the wrinkle is smoothed out.

In the step (a), a volume-to-volume ratio of water to the non-water-soluble liquid is preferably 5:1 to 1:10, more preferably 1:1 to 1:5, and particularly preferably 2:3 to 1:3.

The composition used in the step (a) (and the obtained first emulsion) contains the recombinant gelatin preferably in an amount of 1% to 15% by weight, more preferably in an amount of 1.5% to 10% by weight, and particularly preferably in an amount of 3% to 5% by weight, contains water preferably in an amount of 10% to 70% by weight, more preferably in an amount of 20% to 50% by weight, and particularly preferably in an amount of 30% to 40% by weight, contains the non-water-soluble liquid preferably in an amount of 20% to 90% by weight, more preferably in an amount of 40% to 80% by weight, and particularly preferably in an amount of 50% to 70% by weight, and contains the emulsifier preferably in an amount of 0.5% to 20% by weight, more preferably in an amount of 1% to 10% by weight, and particularly preferably in an amount of 2% to 6% by weight.

The step (a) is preferably performed at a temperature of 10° C. to 100° C., more preferably at a temperature of 20° C. to 80° C., and particularly preferably at a temperature of 30° C. to 60° C.

The mixing performed in the step (a) and the step (b) may be conducted by any suitable method. For example, the mixing can be performed by shaking or stirring. It is preferable to performing the mixing by stirring. Particularly, when a dissolving machine-type stirring is adopted, the stirring is preferably performed at a speed of 20 to 5,000 revolutions per minute (rpm), more preferably at a speed of 200 to 1,000 rpm, and particularly preferably at a speed of 250 to 600 rpm. The mixing speed in the step (a) may be the same as or different from the mixing speed in the step (b).

In the step (b), a volume-to-volume ratio of the first emulsion to the non-water-soluble liquid mixed with the first emulsion is preferably 5:1 to 1:100, more preferably 2:1 to 1:10, and particularly preferably 1:1 to 1:3.

The second emulsion preferably contains the first emulsion in an amount of 1% to 85% by weight, more preferably in an amount of 10% to 65% by weight, and particularly preferably in an amount of 25% to 50% by weight, and contains the non-water-soluble liquid (that is, the non-water-soluble liquid that is added to the non-water-soluble liquid already existing in the first emulsion in the step (a) and that the second emulsion contains for the first time in the step (b)) in an amount of 15% to 99% by weight, more preferably in an amount of 35% to 90% by weight, and particularly preferably in an amount of 50% to 75% by weight. It is preferable that the non-water-soluble liquid mixed with the first emulsion in the step (b) contains an emulsifier having HLB of less than 8, preferably in an amount of 0% to 0.1% by weight and more preferably in an amount of 0% by weight. It is preferable that the non-water-soluble liquid mixed with the first emulsion in the step (b) does not contain an emulsifier.

It is preferable that the step (b) is performed at a temperature higher than a gelation temperature of the gelatin. The gelation temperature of the gelatin can be determined by any suitable method. For example, it is possible to use the method described in "Tosh et al in Applied Physics Letters, Vol. 84, Number 21, 24 May 2004". Particularly, it is possible to use the third method described in the above document. The gelation temperature depends on the identity of the gelatin and the degree of concentration of the gelatin.

It is preferable that the step (b) is performed at a temperature which is 1° C. to 80° C., preferably 3° C. to 70° C., and particularly preferably 5° C. to 60° C. higher than the gelation temperature of the gelatin.

Generally, the step (b) is performed at a temperature of 10° C. to 100° C., for example, at a temperature within a range of 15° C. to 70° C. and particularly at a temperature within a range of 20° C. to 60° C., although the temperature depends on the gelatin.

In reality, generally, it is not important to ascertain the gelation temperature of the gelatin with high accuracy. It is enough to roughly know the gelation temperature, because the step (b) can be performed at a temperature sufficiently higher than the gelation temperature at which gelation clearly occurs simply by roughly ascertaining the gelation temperature through calculation without actually measuring the gelation temperature.

The cooling performed in the step (c) may be passive or active. For example, the passive cooling can be performed simply by allowing the second emulsion to be spontaneously cooled down to the temperature at which the gelatin coagulates. The active cooling can be performed by using a cooling method (for example, ice or ice water) for lowering the temperature (at a controlled cooling rate, for example) of the second emulsion. The active cooling is useful for adjusting the properties of the final microcarriers.

In the step (c), it is preferable that the second emulsion is cooled at a rate of 0.1° C. to 20° C./min and more preferably at a rate of 1° C. to 10° C./min. By the aforementioned cooling rate, the microcarriers having particularly useful characteristics can be provided. For example, in a case where the second emulsion has a temperature of 60° C., a preferred cooling rate is 1.8° C./min. After 30 minutes, the final temperature of the obtained mixture becomes 6° C. The cooling rate may be linear or nonlinear.

The method of the present invention preferably further includes (d) a step of removing coagulated gelatin from the second emulsion and preferably removing coagulated gelatin by filtration.

Considering the matters described so far, the method as a first present invention preferably has the following characteristics.

(i) The composition used in the step (a) contains the recombinant gelatin in an amount of 3% to 5% by weight, water in an amount of 30% to 40% by weight, the non-water-soluble liquid in an amount of 50% to 70% by weight, and the emulsifier in an amount of 2% to 6% by weight, (ii) the mixing in each of the step (a) and the step (b) is performed by stirring at a speed of 250 to 600 rpm, (iii) the volume-to-volume ratio of water to the non-water-soluble liquid in the step (a) is within a range of 2:3 to 1:3, (iv) the step (a) is preferably performed at a temperature within a range of 30° C. to 60° C., (v) the composition used in the step (b) contains the first emulsion in an amount of 25% to 50% by weight and the non-water-soluble liquid in an amount of 50% to 75% by weight, and the non-water-soluble liquid does not contain an emulsifier, (vi) the step (c) is preferably performed such that the second emulsion is cooled at a ratio of 1° C. to 10° C./min, and (vii) the method of the present invention arbitrarily further includes a step of cross-linking the obtained recombinant gelatin microcarriers and preferably a step of cross-linking the microcarriers by thermal dehydration cross-linking.

According to a second present invention, there are provided porous recombinant gelatin microcarriers having one or more of the following characteristics. Furthermore, the porous gelatin microcarriers of the present invention preferably have one or more of the following characteristics.

(a) Surface pores having a mean diameter of at least 5 μm, for example, 6 to 30 μm, and particularly, 10 to 20 μm. It is preferable that the surface pores have a mean diameter that is less than 5% of the particle size of the microcarriers.

(b) A mean void volume of at least 50% by volume, for example, 51% to 95% by volume, and particularly, 60% to 90% by volume (c) A mean particle size of 20 to 800 μm, for example, 40 to 600 μm, and particularly, 100 to 500 μm (d) A mean density of 0.04 to 0.50 g/cm$^3$, for example, 0.06 to 0.25 g/cm$^3$, and particularly, 0.1 to 0.2 g/cm$^3$ (e) A tapped volume of 2 to 25 cm$^3$/g, for example, 4 to 17 cm$^3$/g, and particularly, 5 to 10 cm$^3$/g (f) A mean particle size of 20 to 800 μm. At least 80% of the microcarriers have a particle size that is 30% to 200% of the mean particle size.

The mean particle size is a volume-weighted mean diameter, and can be measured using a Malvern Mastersizer.

The mean diameter of the surface pores can be measured through micro-computed tomography (CT) image analysis. For example, it is possible to use a Skyscan 1172 MicroCT apparatus (manufactured by Bruker microCT), and it is preferable that the apparatus includes VGStudio MAX 2.2 software.

The mean void volume of the microcarriers is defined by the following Formula (1)

$$P = (pvI/V) \times 100\%$$  Formula (1)

Herein, P is a mean void volume, pvI is a mean volume of total space in the microcarriers, and V is a total volume of microcarriers and also includes a spatial volume.

pvI can be measured by micro-CT scanning (for example, a Skyscan 1172 MicroCT apparatus (manufactured by Bruker microCT) can be used, and it is preferable that the apparatus includes VGStudio MAX 2.2 software).

V can be calculated by measuring the volume of the microcarriers (for example, by using the size of the microcarriers that is determined by the image analysis using micro CT scanning), and mathematically calculating the mean volume.

It is preferable that the recombinant gelatin microcarriers obtained by the method as the first present invention one or more of the characteristics (a) to (f) described above and/or one or more of the following characteristics relating to a third present invention. By the method as the first present invention, the porous recombinant gelatin microcarriers can be obtained. The characteristics (a) to (f) can be applied to both of the cross-linked microcarriers of the present invention and the non-cross-linked microcarriers of the present invention. In order to obtain gelatin microcarriers having a three-dimensional structure totally different from the commercially available microcarriers that are on the market, the method of the present invention can be used.

According to the third present invention, it is possible to provide porous recombinant gelatin microcarriers that have voids having a mean diameter which is 5% to 25% (preferably 10% to 20%) of the particle size of the microcarriers. In the porous recombinant gelatin microcarriers and the porous gelatin microcarriers of the present invention, the voids preferably bind to adjacent voids through pores. The mean diameter of the voids is preferably within a range of 5% to 25% of the mean particle size of the microcarriers. In order to allow biological cells to enter the voids, it is preferable that at least half, more preferably at least 75%, and particularly preferably 90% of the voids are sufficiently connected to each other and to the outside (for example, through the pores) of the microcarriers. It is preferable that the voids have a porous wall (for example, a wall having holes) that enables biological cells to enter the voids. The pores (or holes) on the wall of the voids preferably have a mean diameter of at least 5 μm and more preferably have a mean diameter of at least 10 μm.

It is preferable that at least half, more preferably at least 75%, and particularly preferably 80% of the voids have a diameter that is −30% to +30% of the mean diameter of the voids. Furthermore, it is preferable that at least half, more preferably at least 75%, and particularly preferably 80% of the voids are spherical. In addition, it is preferable that at least half, more preferably at least 75%, and particularly preferably 80% of the voids have a recessed wall. In this way, the gelatin microparticles can provide a plurality of scaffolds featuring spherical voids/recessed wall, and pores/holes that allow cells or pharmaceutical substances to enter the voids when, for example, two voids overlap each other.

The gelatin used for preparing microcarriers having voids is preferably recombinant gelatin, and regarding other present inventions, the gelatin is particularly preferably recombinant gelatin described herein.

The present inventions each provides microcarriers or provide microcarriers in combination of two of the present inventions. On average, the present invention provides a plurality of microcarriers (at least 500 mg of microcarriers as one batch) having the properties described above. The gelatin microcarriers of the present invention may have any shape, but the method of the present invention is particularly suitable for preparing spherical particles. In this way, the microcarriers obtained by the method of the present invention preferably have the shape of a sphere, for example, a microsphere.

According to a fourth present invention, there is provides a composite material containing porous microcarrier of gelatin and cells, in which the cells exist on the surface and/or on the inside of the microcarriers. The microcarriers are porous gelatin microcarriers of the present invention or the porous recombinant gelatin microcarriers of the present invention.

The type of the cells according to the composite material of the present invention is not limited, and include human or animal cells. For example, skin cells can be used, and the obtained composite material can be used for treating various types of skin damages. Examples of the cells also include myoblasts (myocytes) that can be used for treating myocardial infarction, and undamaged liver cells that can be used for a toxic substance in a lesion in the liver. In a suitable embodiment, the cells include stem cells such as embryonic stem cells, hematopoietic stem cells, stem cells of neurons, epidermal stem cells, and mesenchymal stem cells. Other usable cells include pluripotential cells, endothelial cells, precursor cells, and bone marrow-derived cells.

The composite material of the present invention can be prepared by culturing desired cells and microcarriers. Generally, a suspension containing microcarriers and desired cells is mixed with nutrients in a culture vessel. The culture vessel used depends on the manufacturing scale. For small-scale manufacturing, a stirring vessel suited for a small laboratory can be used. For large-scale manufacturing, a tank having thousands of tons of volume can be used.

The nutrients are generally selected according to the cells to be grown, and a mixture of many nutrients and mecia can be commercially available. For example, it is possible to use a Dulbecco's modified eagle's medium (DMEM), basal medium eagle (BME), a DMEM/F12 medium, Ham's F-10 and F-12 media, a medium 199, MEM, Ames' media, a BGjb medium (Fitton-Jackson Modification), a Click's medium, a CMRL-1066 medium, Fischer's medium, a Glascow Minimum Essential Medium (GMEM), an Iscove's Modified Dulbecco's Medium (IMDM), an L-15 Medium (Leibovitz), a McCoy's 5A Modified Medium, an NCTC Medium, a Swim's S-77 Medium, a Waymouth Medium, and William's Medium E and RPMI 1640 Media.

The microcarriers of the present invention can be used for various purposes as scaffolds for tissue damage repair, for example, as cell carriers. Accordingly, the microcarriers can be used for culturing artificial skin, artificial tissues, adipocytes, muscles, blood vessels, and the like. The microcarriers can be used as both of the cell carriers for cell culture and the cell carriers surviving for producing a desired substance before and after the microcarriers are transplanted into the body of a human being or animal. The cells may be the cells of the host (autotransplantation) or the cells (homologous or heterologous) from other sources. In some cases, it is possible to grow the cells as desired products, for example, the adipocytes (preadipocytes) on the carriers at the initial stage after transplantation such the cells are converted into adipocytes. One of the fields in which the microcarriers are used is, for example, cosmetic surgery.

The microcarriers of the present invention can also be transplanted into the body of a human being or animal without adding cells to the microcarriers. After the transplantation, the nearby cells in the body move to the microcarriers and form colonies. After the transplanted microcarriers degrade, the cells that have formed the colonies form a structure as intended by the transplantation. According to a fifth present invention, it is possible to provide a composition for injection containing a pharmacologically acceptable carrier, and the microcarriers or composition of the present invention.

It is preferable that the composition can be injected through a syringe having an internal caliber of 80 to 4,000 µm. The pharmacologically acceptable suitable carrier includes a liquid such as water, ethanol, and a mixture containing water and/or ethanol. It is preferable that the pharmacologically acceptable carrier is sterile, and the carrier can optionally contain a preservative.

EXAMPLES

Hereinafter, the present invention will be described based on examples, but the present invention is not limited thereto.

Hereinafter, the abbreviations described below will be used.

"RG1" means a 10% by weight RGD-enriched recombinant gelatin solution (MWT: 51.2 kDa) having a pH of 5.4. Based on a modified nucleic acid sequence which encodes the portion of an amino acid sequence of human COL1A1-I gelatin, gelatin was prepared. The methods described in EP-A-0926543, EP-A-1014176, WO01/34646 were used. The gelatin does not contain hydroxyproline and has the following amino acid sequence of SEQ ID NO: 1. Amino acid sequence of SEQ ID NO: 1:

GAPGAPGLQGAPGLQGMPGERGAAGLPGPKGERGDAGPKGADGAPGAPGL

QGMPGERGAAGLPGPKGERGDAGPKGADGAPGKDGVRGLAGPIGPPGERG

AAGLPGPKGERGDAGPKGADGAPGKDGVRGLAGPIGPPGPAGAPGAPGLQ

GMPGERGAAGLPGPKGERGDAGPKGADGAPGKDGVRGLAGPPGAPGLQGA

PGLQGMPGERGAAGLPGPKGERGDAGPKGADGAPGAPGLQGMPGERGAAG

LPGPKGERGDAGPKGADGAPGKDGVRGLAGPIGPPGERGAAGLPGPKGER

GDAGPKGADGAPGKDGVRGLAGPIGPPGPAGAPGAPGLQGMPGERGAAGL

PGPKGERGDAGPKGADGAPGKDGVRGLAGPPGAPGLQGAPGLQGMPGERG

AAGLPGPKGERGDAGPKGADGAPGAPGLQGMPGERGAAGLPGPKGERGDA

GPKGADGAPGKDGVRGLAGPIGPPGERGAAGLPGPKGERGDAGPKGADGA

PGKDGVRGLAGPIGPPGPAGAPGAPGLQGMPGERGAAGLPGPKGERGDAG

PKGADGAPGKDGVRGLAGPPG;

The SEQ ID NO: 1 has a length consisting of 571 amino acids, and includes 12 RGD motifs.

"RG2" is the same as "RG1", except that the amount of gelatin contained in RG2 is not 10% by weight but 4% by weight.

"RG3" is the same as "RG1", except that the amount of gelatin contained in RG3 is not 10% by weight but 15% by weight.

"Tween (registered trademark) 80" is a polyoxyethylene sorbitan oleic acid monoester.

"PBS" is phosphate-buffered saline.
"DAPI" is 4',6-diamidino-2-phenylindole (for cell staining).

Example 1

Step (a) Preparation of First Emulsion

A mixture of RG1 (15 g) and Tween 80 (1.0 g) was heated to 60° C. and kept at the same temperature for 15 minutes. While the mixture was being stirred at 550 rpm, a non-water-soluble liquid (corn oil, 30 cm³) was added thereto for 7 minutes. In a state where the temperature was kept at 60° C., the resultant was stirred 3 more minutes at 550 rpm, thereby obtaining a first emulsion.

Step (b) Preparation of Second Emulsion

In a state where a non-water-soluble liquid (corn oil, 55 cm³) was being stirred at 350 rpm, the first emulsion was added dropwise thereto for 3 minutes. When the addition was finished, the resultant was stirred 3 more minutes at 20° C., thereby obtaining a second emulsion.

Step (c) Cooling of Second Emulsion

After the 3 minutes of stirring described in the step (b), the second emulsion was kept stirred at 350 rpm and cooled in this state to 5.5° C. for 5 minutes. When the temperature of the mixture became 5.5° C., the mixture was further stirred for 15 minutes at the same temperature. By using an ice bath, a vessel containing acetone (300 ml) was cooled to a temperature of +1° C. to −1° C. Then, in a state of being stirred at 350 rpm, the second emulsion was added to the cooled acetone. After the mixture was stirred for 5 minutes at 350 rpm, the vessel was taken out of the ice bath, and the mixture was kept stirred for 1 hour at room temperature. As a result, by the acetone, the microcarriers formed in the mixture were dehydrated. The microcarriers were separated by filtration and washed several times with acetone until water and the corn oil were removed from the microcarriers. The microcarriers were then dried in an oven at a temperature of 60° C.

Optional Step (d) Cross-Linking

The microcarriers obtained through the step (c) were cross-linked by the following thermal dehydration treatment.

The dried microcarriers were put into a glass vial and placed in a Binder VD53 vacuum stove in a vacuum for 96 hours at a temperature of 145° C. The obtained porous recombinant gelatin microcarriers were named MS1, and the characteristics are described in the following Table 1 (characteristics of microcarriers MS1). At least half of the voids in the MS1 were spherical and had a diameter that was −30% to +30% of the mean diameter of the voids.

TABLE 1

| Mean void diameter (µm) | Mean void volume (%) | Mean particle size (µm) | Mean density (g/cm³) | Mean volume (cm³/g) |
|---|---|---|---|---|
| 45 | 85 | 277 | 0.17 | 6 |

The mean void diameter and the shape were determined by cutting the microcarriers and analyzing the cross-section by using micro CT data (obtained by using a Skyscan 1172 MicroCT apparatus including VGStudio MAX 2.2 software manufactured by Bruker microCT) (see FIG. 1C).

The mean void volume was determined by the Formula (1) described above.

The mean particle size is a volume-weighted mean diameter of the microcarriers, and was calculated using a Malvern Mastersizer.

The mean density of the microcarriers was calculated and determined by measuring the total volume (including the voids and the space between spheres) of 1 g of the microcarriers and dividing 1 g by the total volume of the microcarriers.

The mean volume of the microcarriers was determined by measuring the volume (including the voids and the space between the spheres) of 1 g of the microcarriers.

Examples 2 to 9 and Comparative Example 1

Example 1 was repeated by applying the change shown in the following Table 2. The characteristics of the obtained microcarriers are shown in Table 3. In all of the microcarriers MS2 to MS9, at least half of the voids were spherical and has a diameter of −30% to +30% of the mean void diameter. In contrast, in none of CMS1 and Cultispher G, at least half of the voids were spherical and has a diameter of −30% to +30% of the mean void diameter.

TABLE 2

| Example | What changed from Example 1 | Microcarriers |
| --- | --- | --- |
| Example 2 | Step (a) was performed at 45° C. | MS2 |
| Example 3 | Step (a) was performed at 75° C. | MS3 |
| Example 4 | Step (a) was performed using 20 cm³ of corn oil. | MS4 |
| Example 5 | Step (a) was performed using 40 cm³ of corn oil. | MS5 |
| Example 6 | Step (a) was performed using 0.5 g of Tween 80. | MS6 |
| Example 7 | Step (a) was performed using 2 g of Tween 80. | MS7 |
| Example 8 | Step (a) was performed using RG2. | MS8 |
| Example 9 | Step (a) was performed using RG3. | MS9 |
| Comparative Example 1 | In step (b), corn oil (Span 85) containing 5% by weight of emulsifier having HLB of less than 8 was used. | CMS1 |

TABLE 3

| Microcarriers | Mean void diameter (μm) | Mean void volume (%) | Mean particle size (μm) | Mean density (g/cm³) | Mean volume (cm³/g) |
| --- | --- | --- | --- | --- | --- |
| MS2 | 54 | 84 | 295 | 0.20 | 5 |
| MS3 | 25 | 83 | 320 | 0.11 | 9 |
| MS4 | 42 | 79 | 295 | 0.12 | 9 |
| MS5 | 51 | 85 | 330 | 0.11 | 9 |
| MS6 | 50 | 82 | 280 | 0.13 | 8 |
| MS7 | 25 | 84 | 295 | 0.10 | 10 |
| MS8 | 48 | 88 | 270 | 0.07 | 14 |
| MS9 | 20 | 78 | 295 | 0.1 | 10 |
| CMS1 | * | 83 | 290 | 0.08 | 12 |
| Cultispher G | * | 64 | 180 | 0.38 | 3 |

The mean void diameter, the mean void volume, the mean particle size, the mean density, and the mean volume were measured as described in Example 1.

In the table, * shows that the mean void diameter could not be measured because the voids of CMS1 or Cultispher G were not spherical.

The samples MS1 and CMS1 and the commercially available CultiSpher G were analyzed using a scanning electron microscopy (SEM). The obtained images are shown in drawings. FIGS. 1A to 1C show MS1, FIGS. 2A to 2C show Comparative Example CMS1, and FIGS. 3A to 3C show the commercially available CultiSpher G.

The drawings show that MS1 microcarriers are excellently separated from each other and substantially have a spherical shape having spherical voids excellently differentiated from each other. In contrast, the microcarriers CMS1 of comparative example have a non-spherical shape, have large surface holes, and for a secondary structure by being lumped together. FIG. 2C shows a cross-section of the microcarriers obtained by the method of the comparative example. FIG. 2C shows that the voids are smaller than the particle size of the microparticles, compared to the microcarriers of the present invention shown in FIG. 1A. Furthermore, the voids of the microparticles shown in FIG. 2C have irregular size and shape.

Preparation of Microcarriers-Cell Composition and Test Cell Growth Measured by Staining A synthetic material containing the cross-linked porous microcarrier of gelatin described in the above examples and comparative example was prepared as below.

Sterilization Step

At the evaluation stage, the microcarriers (100 mg) were each put in phosphate-buffered saline (PBS, 10 cm³, free of calcium and magnesium), allowed to stand for 1 hour at room temperature, and then sterilized using an autoclave without removing PBS. After the sterilization, PBS was removed, and then PBS was newly added thereto. This cycle was repeated 3 times. The finally obtained sterilized microcarriers were stored in a DMEM medium containing 10% fetal bovine serum (FBS) at 4° C. until they were used.

Preparation of C2C12 cells (mouse myofibroblasts, ATCC CRL 1772)

The cells were pre-cultured in a T75 culture flask and densely populated to 50% to 60%. When actively growing, the cells were subcultured. The cells were rinsed with PBS (1 ml/5 cm²), and the DMEM medium containing 10% fetal bovine serum (FBS) was removed. A trypsin/EDTA solution was added to the cells (3 to 4 ml/75 cm²), followed by incubation for 6 minutes at 37° C. A complete medium was added and used at a ratio of 1:2 with respect to the amount of trypsin, thereby neutralizing trypsin. The obtained single-cell solution was subjected to centrifugation for 5 minutes at 125 rpm. The supernatant was collected, and the cells in the obtained cell pellets were resuspended well in a DMEM medium containing 10% FBS. The cell density was determined using a microscope.

Spinner Flask Culture

A 25 ml sterile spinner flask (Wheaton) was washed with pure water (10 cm³), and the microspheres (40 mg) dried at the evaluation stage were added to the spinner flask. The flask was filled up with the DMEM/10% FBS medium for cell culture such that the end volume thereof became 8 ml. The flask was left for 30 minutes in an incubator such that equilibrium is established. Then, the aforementioned C2C12 cells ($2\times10^6$ cells/2 cm³) were added to the culture medium. The obtained mixture was stirred for 5 minutes at 50 rpm, the stirring was stopped, and the mixture was left to stand for 40 minutes. In this cycle, the mixture was stirred for 3 hours. The cycle was performed 4 times. Thereafter, a portion of the culture medium (10 cm³) was added thereto, and the cells were cultured for 7 days in a humidified incubator under the conditions of 37° C., 5% $CO_2$, and 80 rpm. The culture medium was removed by 50% every day and replaced with an unused culture medium.

Analysis

Seven days after the cell culture, the obtained synthetic material (microcarriers+cells) was stained with DAPI. When binding to double-stranded DNA, DAPI has absorption maximum at a wavelength of 358 nm (ultraviolet rays), and an emission maximum thereof is 461 nm (blue). The nuclei of the cells can be seen as spots highlighted in blue. The number of nuclei of the cells were counted, and the number showed a degree of cell growth relating to the cross-linked microcarriers. Through the SEM analysis of the cross-section of the spheres after the cell culture, the degree of cell growth in the microcarriers were clarified. The outer surface of the microcarriers was slightly stained as well. The results are shown in Table 4 (results of growth evaluated by DAPI staining).

TABLE 4

| Cross-linked microcarriers | Cell growth score (by visual examination after staining method) |
| --- | --- |
| MS1 | +++ |
| MS2 | +++ |
| MS3 | ++ |
| MS4 | ++ |
| MS5 | ++ |
| MS6 | +++ |
| MS7 | ++ |
| MS8 | ++ |
| MS9 | ++ |
| CultispherG | + |
| CMS1 | + |

In Table 4, the following scores were used.

"+++" means "extremely excellent cell growth" determined by visual examination.

"++" means "excellent cell growth" determined by visual examination.

"+" means "normal cell growth" determined by visual examination.

As is evident from Table 4, cell growth was better in examples than in the comparative examples of CMS1 and CultiSpher G.

SEQUENCE LIST

Method for preparing microcarriers of international application 15F03330 accepted based on Patent Cooperation Treaty, MaJP15079787 20151022----000701407515021152253normal20151022115444220150-9141117056210_P1AP10 1_15_4.app

What is claimed is:

1. Porous gelatin microcarriers having voids,
wherein the gelatin is recombinant gelatin containing RGD-enriched motifs and the gelatin does not contain hydroxyproline,
at least half of the voids are spherical, and
at least half of the voids have a diameter that is −30% to +30% of a mean diameter of the voids.

2. The microcarriers according to claim 1 that have surface pores having a mean diameter of at least 5 μm.

3. The microcarriers according to claim 1 that have a mean void volume of at least 50% by volume.

4. The microcarriers according to claim 1,
wherein a mean diameter of the voids is within a range of 5% to 25% of a mean particle size of the microcarriers.

5. The microcarriers according to claim 1 that have a mean particle size of 20 to 800 μm.

6. The microcarriers according to claim 1 that have a mean density of 0.04 to 0.5 g/cm³.

7. The microcarriers according to claim 1 that have a mean particle size of 20 to 800 μm,
wherein at least 80% of the microcarriers have a particle size that is 30% to 200% of the mean particle size.

8. The microcarriers according to claim 1, in which at least 75% of the voids are spherical.

9. The microcarriers according to claim 1, in which the gelatin is recombinant gelatin having at least an isoelectric point of 5.

10. The microcarriers according to claim 1, in which the gelatin is recombinant gelatin containing at least 3 RGD motifs.

11. The microcarriers according to claim 1, in which the gelatin is recombinant gelatin that contains at least two lysine residues, the two lysine residues are extreme lysine residues, a first extreme lysine residue is a lysine residue closest to an N-terminal of the gelatin, a second extreme lysine residue is a lysine residue closest to a C-terminal of the gelatin, and the extreme lysine residues are separated from each other by at least 25% of a total number of amino acid residues in the gelatin.

12. The microcarriers according to claim 1 that have surface pores having a mean diameter of at least 5 μm, a mean void volume of at least 50% by volume, and a mean particle size of 20 to 800 μm, in which at least half or more of the voids are spherical, at least 80% of the microcarriers have a particle size that is 30% to 200% of the mean particle size, and a mean diameter of the voids is within a range of 5% to 25% of the mean particle size of the microcarriers.

13. The microcarriers according to claim 1 that have surface pores having a mean diameter of at least 5 μm, a mean void volume of at least 50% by volume, and a mean particle size of 20 to 800 μm, in which at least half or more of the voids have a diameter that is −30% to +30% of a mean diameter of the voids, at least 80% of the microcarriers have a particle size that is 30% to 200% of the mean particle size of the microcarriers, and the mean diameter of the voids is within a range of 5% to 25% of the mean particle size of the microcarriers.

14. A composite material comprising:
the microcarriers according to claim 1; and
cells,
wherein the cells exist on a surface and/or on the inside of the microcarriers.

15. A composition for injection, comprising:
a pharmacologically acceptable carrier; and
the microcarriers according to claim 1.

16. The composition for injection according to claim 15 that can be injected through a syringe having an internal diameter of 80 to 4,000 μm.

* * * * *